United States Patent
Biedermann et al.

(12)

(10) Patent No.: US 9,895,172 B2
(45) Date of Patent: Feb. 20, 2018

(54) RECEIVING PART FOR RECEIVING A ROD FOR COUPLING THE ROD TO A BONE ANCHORING ELEMENT

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 14/878,809

(22) Filed: Oct. 8, 2015

(65) Prior Publication Data

US 2016/0135847 A1    May 19, 2016

Related U.S. Application Data

(63) Continuation of application No. 12/855,395, filed on Aug. 12, 2010, now Pat. No. 9,283,000.

(Continued)

(30) Foreign Application Priority Data

Aug. 12, 2009  (EP) .................................... 09167751

(51) Int. Cl.
*A61B 17/70*    (2006.01)

(52) U.S. Cl.
CPC ...... *A61B 17/7037* (2013.01); *A61B 17/7032* (2013.01)

(58) Field of Classification Search
CPC .................. A61B 17/7032; A61B 17/7037
See application file for complete search history.

(56) References Cited

U.S. PATENT DOCUMENTS 5,669,911 A * 9/1997 Errico ................ A61B 17/7037
606/264
5,672,176 A * 9/1997 Biedermann ...... A61B 17/7037
606/271

(Continued)

FOREIGN PATENT DOCUMENTS

JP      2007-502677 A    2/2007
WO   WO 2005/018471 A1   3/2005

(Continued)

OTHER PUBLICATIONS

Office action issued by the USPTO dated Dec. 5, 2011 for U.S. Appl. No. 12/709,375, 7 pages.

(Continued)

*Primary Examiner* — Ellen C Hammond
*Assistant Examiner* — Stuart S Bray
(74) *Attorney, Agent, or Firm* — Lewis Roca Rothgerber Christie LLP

(57) ABSTRACT

A receiving part for receiving a rod for coupling the rod to a bone anchoring element includes a receiving part body including a first end and a second end, and having a substantially U-shaped recess at the first end forming a channel for receiving the rod, and an accommodation space for accommodating a head of the bone anchoring element, the accommodation space having an opening at the second end for introducing the head; and a pressure element arranged at least partially in the accommodation space, the pressure element including a first section having a second recess for receiving the rod, and a second section having a flexible portion to clamp the head, the first section and the second section being fixed relative to each other, wherein said pressure element is insertable from the opening.

22 Claims, 3 Drawing Sheets

Related U.S. Application Data

(60) Provisional application No. 61/233,406, filed on Aug. 12, 2009.

(56) References Cited

U.S. PATENT DOCUMENTS

| | | | | |
|---|---|---|---|---|
| 5,797,911 | A * | 8/1998 | Sherman | A61B 17/7037 606/266 |
| 5,879,350 | A * | 3/1999 | Sherman | A61B 17/7037 606/266 |
| 6,053,917 | A | 4/2000 | Sherman et al. | |
| 6,063,090 | A * | 5/2000 | Schlapfer | A61B 17/7041 606/270 |
| 6,280,442 | B1 * | 8/2001 | Barker | A61B 17/7037 606/256 |
| 6,368,321 | B1 * | 4/2002 | Jackson | A61B 17/7032 606/270 |
| 6,371,957 | B1 * | 4/2002 | Amrein | A61B 17/7032 606/270 |
| 6,471,705 | B1 * | 10/2002 | Biedermann | A61B 17/7032 606/271 |
| 6,626,906 | B1 * | 9/2003 | Young | A61B 17/7037 606/278 |
| 7,186,255 | B2 * | 3/2007 | Baynham | A61B 17/7035 606/266 |
| 7,211,087 | B2 | 5/2007 | Young | |
| 7,322,981 | B2 * | 1/2008 | Jackson | A61B 17/7037 606/266 |
| 7,604,655 | B2 * | 10/2009 | Warnick | A61B 17/7032 606/265 |
| 7,803,174 | B2 * | 9/2010 | Denis | A61B 17/7035 606/250 |
| 7,896,902 | B2 * | 3/2011 | Jeon | A61B 17/7032 606/246 |
| 7,942,910 | B2 * | 5/2011 | Doubler | A61B 17/7037 606/265 |
| 8,016,862 | B2 * | 9/2011 | Felix | A61B 17/7032 606/266 |
| 8,021,398 | B2 * | 9/2011 | Sweeney | A61B 17/7037 606/268 |
| 8,100,909 | B2 * | 1/2012 | Butler | A61B 17/7035 606/151 |
| 8,100,946 | B2 * | 1/2012 | Strausbaugh | A61B 17/7032 606/266 |
| 8,197,517 | B1 * | 6/2012 | Lab | A61B 17/7037 606/268 |
| 8,206,418 | B2 * | 6/2012 | Triplett | A61B 17/7067 606/246 |
| 8,221,472 | B2 | 7/2012 | Peterson et al. | |
| 8,361,122 | B2 | 1/2013 | Barrus et al. | |
| 8,926,671 | B2 * | 1/2015 | Biedermann | A61B 17/7032 606/268 |
| 2003/0023240 | A1 | 1/2003 | Amrein et al. | |
| 2004/0116929 | A1 | 6/2004 | Barker et al. | |
| 2005/0070901 | A1 * | 3/2005 | David | A61B 17/7041 606/278 |
| 2005/0203516 | A1 * | 9/2005 | Biedermann | A61B 17/701 606/267 |
| 2006/0058788 | A1 * | 3/2006 | Hammer | A61B 17/7034 606/266 |
| 2006/0149244 | A1 | 7/2006 | Amrein et al. | |
| 2006/0247624 | A1 * | 11/2006 | Banouskou | A61B 17/7037 606/60 |
| 2006/0271047 | A1 * | 11/2006 | Jackson | A61B 17/7037 606/304 |
| 2007/0118118 | A1 * | 5/2007 | Kwak | A61B 17/7032 606/279 |
| 2007/0288004 | A1 * | 12/2007 | Alvarez | A61B 17/7032 606/86 A |
| 2008/0015580 | A1 * | 1/2008 | Chao | A61B 17/7037 606/86 A |
| 2008/0161859 | A1 * | 7/2008 | Nilsson | A61B 17/7032 606/266 |
| 2008/0269809 | A1 * | 10/2008 | Garamszegi | A61B 17/7037 606/305 |
| 2008/0294202 | A1 * | 11/2008 | Peterson | A61B 17/7032 606/305 |
| 2009/0105716 | A1 * | 4/2009 | Barrus | A61B 17/7032 606/301 |
| 2010/0198272 | A1 * | 8/2010 | Keyer | A61B 17/7082 606/302 |
| 2010/0234891 | A1 * | 9/2010 | Freeman | A61B 17/7037 606/266 |
| 2011/0276093 | A1 * | 11/2011 | Barrus | A61B 17/7032 606/264 |
| 2012/0035663 | A1 * | 2/2012 | Jackson | A61B 17/7005 606/266 |
| 2012/0253409 | A1 | 10/2012 | Peterson et al. | |
| 2013/0110179 | A1 | 5/2013 | Barrus et al. | |

FOREIGN PATENT DOCUMENTS

| | | |
|---|---|---|
| WO | WO 2009/014540 A1 | 1/2009 |
| WO | WO 2009/015100 A2 | 1/2009 |

OTHER PUBLICATIONS

Office action issued by the USPTO dated Jul. 10, 2012 for U.S. Appl. No. 12/709,375, 6 pages.

Office action issued by the USPTO dated Sep. 13, 2013 for U.S. Appl. No. 12/709,375, 6 pages.

Office action issued by the USPTO dated Jun. 4, 2014 for U.S. Appl. No. 12/709,375, 5 pages.

European Search Report for European Application No. 09167751. 8-1526, European Search Report dated Dec. 15, 2009 and dated Dec. 23, 2009 (6 pgs.).

* cited by examiner

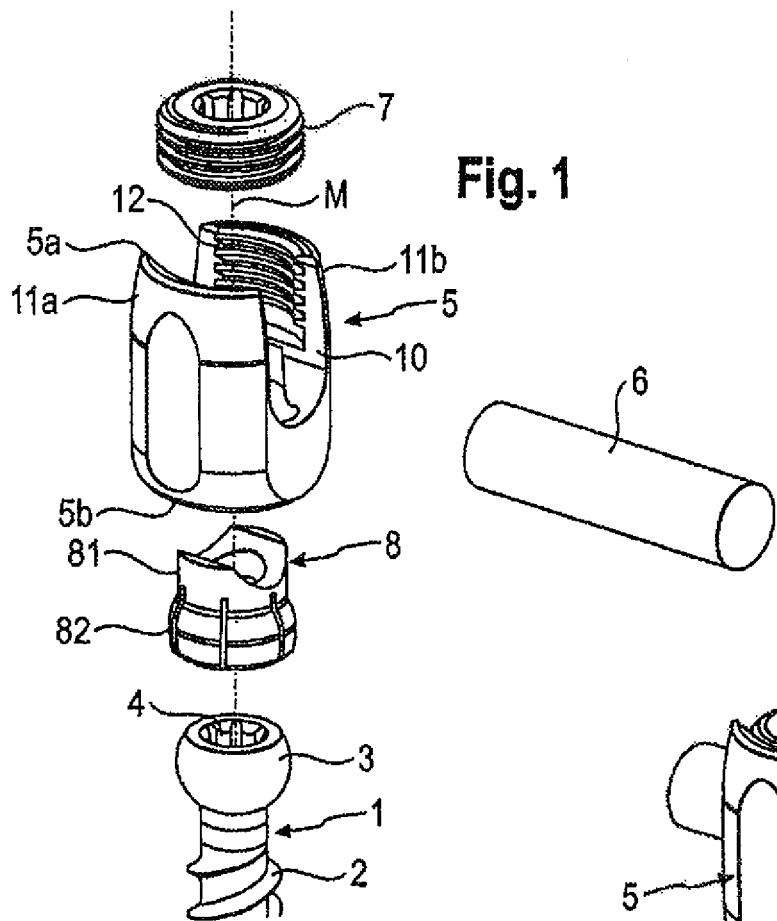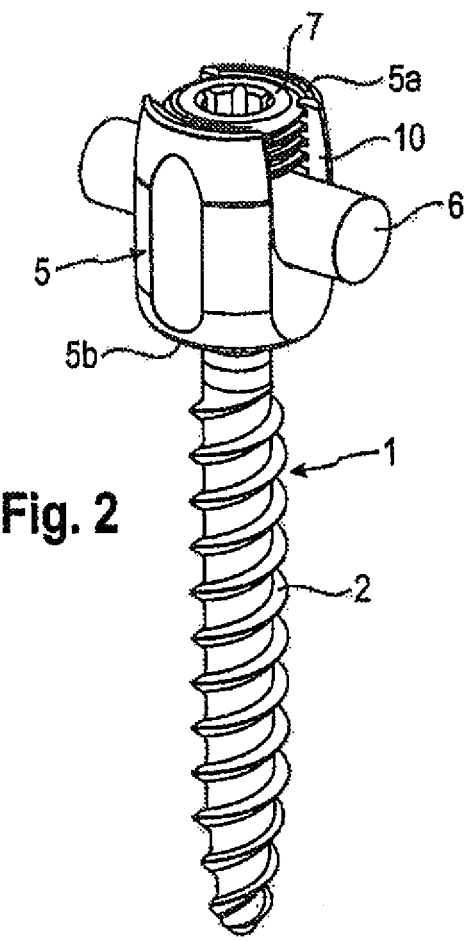

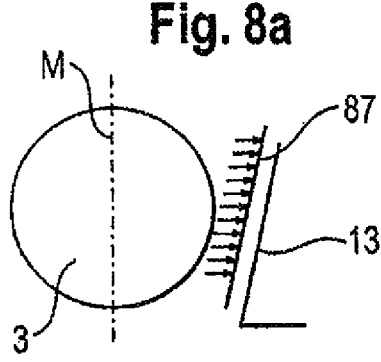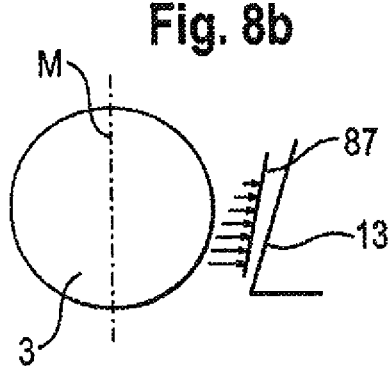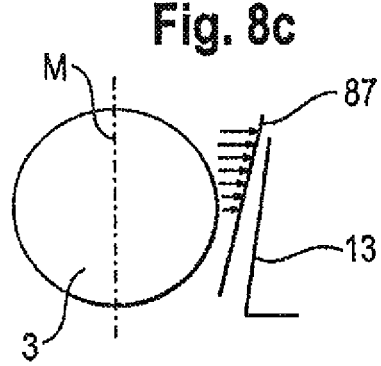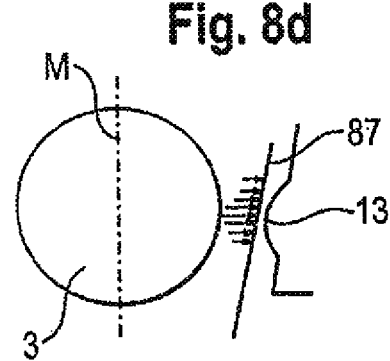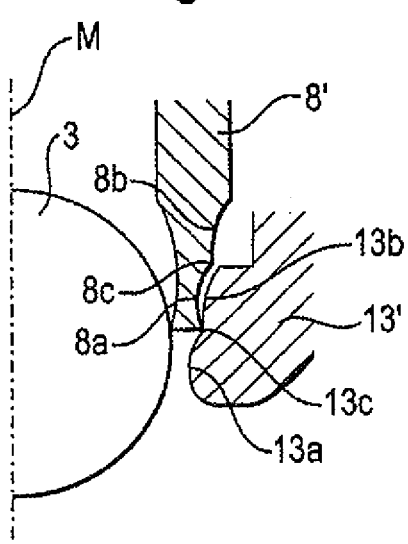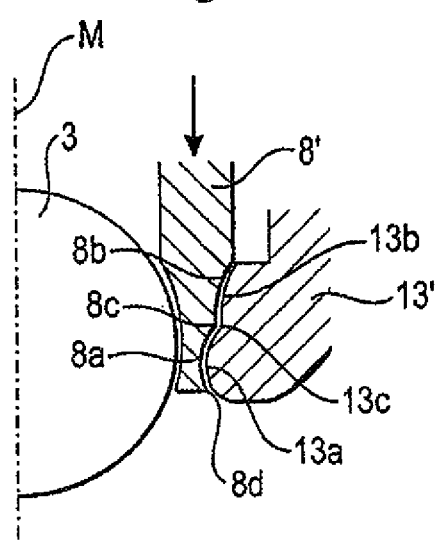

RECEIVING PART FOR RECEIVING A ROD FOR COUPLING THE ROD TO A BONE ANCHORING ELEMENT

CROSS-REFERENCE TO RELATED APPLICATION(S)

This application is a continuation of U.S. patent application Ser. No. 12/855,395, filed Aug. 12, 2010, which claims the benefit of U.S. Provisional Patent Application Ser. No. 61/233,406, filed Aug. 12, 2009, the contents of which are hereby incorporated by reference in their entirety, and claims priority to European Patent Application EP 09 167 751.8, filed Aug. 12, 2009, the contents of which are hereby incorporated by reference in their entirety.

BACKGROUND

Field

The invention relates to a receiving part for receiving a rod for coupling the rod to a bone anchoring element. The receiving part includes a receiving part body with a channel for receiving a rod and an accommodation space for accommodating a head of a bone anchoring element, and a pressure element for clamping the head. The accommodation space has an opening at a bottom side for inserting the pressure element and for inserting the head.

Description of Related Art

Various designs of polyaxial bone screws are known wherein a head is clamped from the side to lock a rotational position of the bone screw.

U.S. Pat. No. 5,672,176 describes a bone screw with a receiving part with a conically shaped seat and a conically shaped pressure element which exerts a pressure onto the head from above and from the side.

U.S. Pat. No. 5,669,911 describes a polyaxial orthopaedic device for use with a rod implant apparatus. The device includes a screw having a curvate head, a locking collar disposed therearound, and a receiving member having a linearly tapered socket in which the screw and the collar are nested. The collar is introduced from the top of the receiving member. The head of the screw can be inserted from the bottom.

U.S. Pat. No. 6,063,090 relates to a device used to connect a longitudinal support to a pedicle screw by an accommodating head having a channel to accommodate the longitudinal support. The pedicle screw and the accommodating head are connected via a conical collate chuck in the accommodating head and by a spherical head on the pedicle screw. The device allows engagement of the pedicle screw in the accommodating head after the pedicle screw has been inserted into the bone.

SUMMARY

Embodiments of the invention provide an improved receiving part for receiving a rod for coupling the rod to a bone anchoring element, and a bone anchoring device with such a receiving part, where the embodiments have fewer parts, a low profile, and provide for improved handling during surgery.

Embodiments of the invention provide a receiving part including a receiving part body including a first end and a second end, and having a substantially U-shaped recess at the first end forming a channel for receiving a rod, and an accommodation space for accommodating a head of a bone anchoring element, the accommodation space having an opening at the second end for introducing the head; and a pressure element arranged at least partially in the accommodation space, the pressure element including a first section having a second recess for receiving the rod, and a second section having a flexible portion to clamp the head, the first section and the second section being fixed relative to each other, wherein said pressure element is insertable from the opening, a bone anchoring device including such a receiving part, and a method of using such a receiving part.

For the receiving part according to an embodiment of the invention, the pressure element has a slim design which allows it to be introduced from the bottom into the receiving part body. An internal end stop within the receiving part body may form an abutment for the pressure element to be positioned in an insertion position for the head. Therefore, there may be no additional components for holding the pressure element in the insertion position.

In some embodiments, the receiving part has a low profile and improved or maximum stiffness, since a wall thickness of the receiving part body can be increased due to the slim design of the pressure element.

BRIEF DESCRIPTION OF THE DRAWINGS

Further features and advantages of the invention will become apparent from the description of embodiments using the accompanying drawings. In the drawings:

FIG. 1 shows a perspective exploded view of a first embodiment of the bone anchoring device.

FIG. 2 shows a perspective view of the bone anchoring device of FIG. 1 in an assembled state.

FIGS. 8a to 8d show schematic views of design modifications of a pressure element and a receiving part body in a locking position according to embodiments of the bone anchoring device.

FIGS. 9a and 9b show schematic views of a further design modification of the pressure element and the receiving portion in a pre-locking position and a locking position, respectively, according to an embodiment of the bone anchoring device.

DETAILED DESCRIPTION

Figure 3:
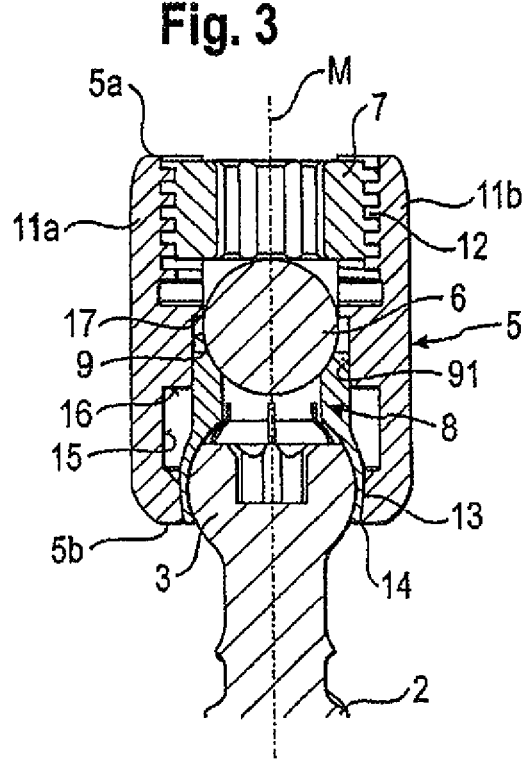
FIG. 3 shows a cross-sectional view of the bone anchoring device of FIG. 1, the section being taken perpendicular to a rod axis.
Figure 4:
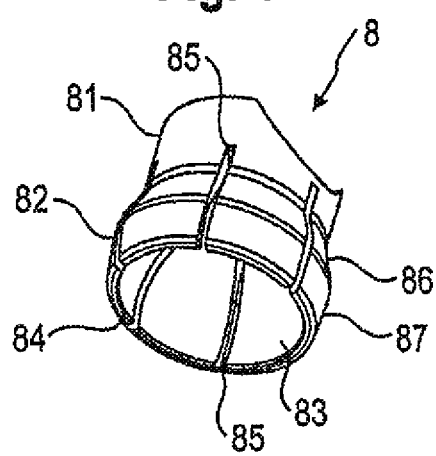
FIG. 4 shows an enlarged perspective view of a pressure element according to an embodiment of the bone anchoring device.
Figure 5:
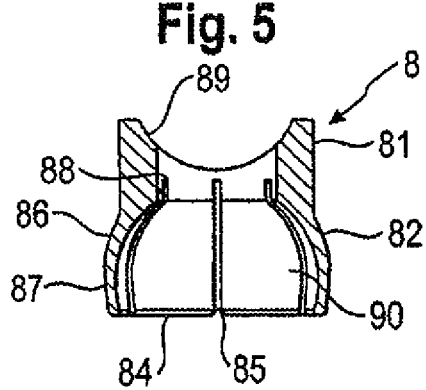
FIG. 5 shows a cross-sectional view of the pressure element according to FIG. 4.
Figure 6:
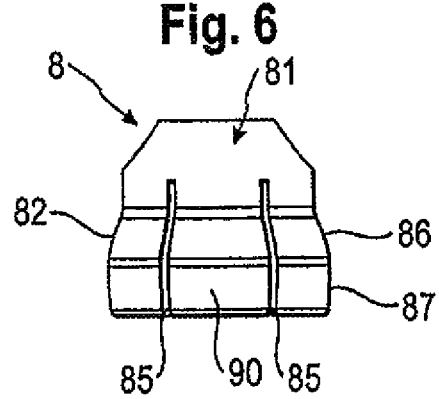
FIG. 6 shows a side view of the pressure element of FIG. 4.
Figure 7:
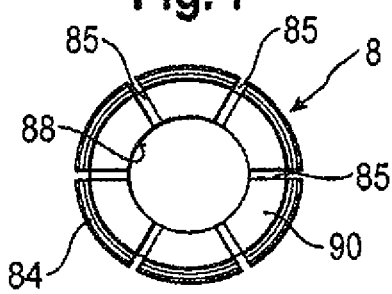
FIG. 7 shows a bottom view of the pressure element of FIG. 4.

As shown in FIGS. 1 and 2, a bone anchoring device according to a first embodiment includes a bone anchoring element 1 in the form of a bone screw having a threaded shaft 2 and a head 3, which in this embodiment is a spherical segment-shaped head. The head 3 has a recess 4 for engagement with a screwing-in tool. The bone anchoring device further includes a receiving part body 5 for receiving a rod 6 to connect the rod to the bone anchoring element 1. Further, a closure element 7, in the form of an inner screw or set screw in some embodiments, is provided for securing the rod 6 in the receiving part body 5. In addition, the bone anchoring device includes a pressure element 8 for locking the head 3 in the receiving part body 5.

The receiving part body 5 is now explained with reference to FIGS. 1 to 3. The receiving part body 5 includes a first end 5*a* and a second end 5*b*, and an axis of symmetry M passes through the first and the second end. A bore 9, which is coaxial with the axis of symmetry M, extends from the first end 5*a* to the second end 5*b*. The bore 9 may have a smallest diameter at, about, or adjacent to its middle section 91 in a center region of the receiving part body 5. In a first region adjacent to the first end 5*a*, the receiving part body 5 has a U-shaped recess 10, which may be symmetric with respect to the symmetry axis M. The recess 10 has a bottom which may be directed towards the second end 5*b* and provides two free lateral legs 11*a*, 11*b* extending towards the first end 5*a*. In the region of the legs 11*a*, 11*b* an internal thread 12 may be provided which may cooperate with the closure element 7, which in this embodiment is a set screw. A channel formed by the U-shaped recess 10 is sized so as to receive the rod 6 therein, the rod for connecting a plurality of bone anchoring devices.

At a second region near the second end 5*b*, the receiving part body 5 has a narrowing portion 13, which narrows in a direction towards the second end 5*b*. The narrowing portion 13 provides a seat for the screw head and the pressure element. The narrowing portion 13 is located at a distance from the second end 5*b* to, for example, enable the screw shaft 2 to be pivoted in a certain pivot angle range. An opening 14 is provided at the second end 5*b*, the diameter of which may be the same as or larger than the diameter of the narrowing portion 13 in some embodiments. Between the narrowing portion 13 and the middle portion 91 of the bore 9, a portion with an inner diameter larger than the diameter of the narrowing portion 13 is provided, which forms a space 15 for allowing the pressure element to expand, as described later. At its side opposite to the narrowing portion 13, the space 15 connects to the middle section 91 of the bore 9 having the smaller diameter, thereby providing a circular shoulder 16.

The middle section 91 of the bore 9 includes a circular projection 17 at its side opposite to the space 15, which can also act as a stop, as described below in more detail.

As can be seen in FIGS. 1 and 3 to 7, a pressure element 8 according to an embodiment of the invention includes a first section 81 which is substantially cylindrical and has an outer diameter which may be slightly smaller than the inner diameter of the middle section 91 of the bore 9, so that the pressure element 8 is movable in the bore 9. It further has a second section 82, which has a hollow interior 83 which is substantially spherically-shaped and is sized to clamp the spherical head 3 therein. The outer diameter of the first section 81 may be, as can be seen in FIG. 3, smaller than an outer diameter of the head 3 and a largest outer diameter of the second section 82 is greater than the outer diameter of the cylindrical section 81. A free end of the second section 82 provides an opening 84 for introduction of the head 3. Further, the second section 82 may have a plurality of slits 85 extending from the edge of the opening 84 through the second section 82 to define or form slightly resilient legs 90. The number and the dimension of the slits 85 may be such that the wall of the second portion is flexible enough to snap onto the head 3 when the head 3 is being inserted. The slits 85 can extend into the first cylindrical section 81 as shown in the figures to enhance flexibility. The outer wall surface of the second section 82 may include a first portion 86 which may be spherically-shaped, and a second portion 87 adjacent to the opening 84 which may be tapered or curved or otherwise narrowing towards the opening 84. The portion 87 cooperates with the narrowing portion 13 of the receiving part body when the head is locked in the receiving part body.

Further, the pressure element has a coaxial bore 88 for providing access to the screw head by a tool. The first section 81 may have at its free end a cylindrically-shaped or cylinder segment-shaped recess 89 for receiving the rod 6 therein.

The dimensions of the pressure element 8 are such that the pressure element 8 can be inserted through the opening 14 at the second end 5*b* of the receiving part body 5, with the cylindrical first section 81 inserted first. When the second section 82 passes through the opening 14, it may be compressed due to the flexibility of the second section 82, or the legs 90 thereof, which allows the pressure element 8 to be fully introduced into the receiving part body 5.

The pressure element 8 can be pushed into the receiving part body 5 until an upper edge of the first section 81 abuts against the stop 17 provided by the annular projection in the receiving part body 5. When the pressure element is in this position, the flexible second section 82 is located in the portion between the middle section 91 of bore 9 and the narrowing portion 13 of the receiving part body 5. In this position, a free space in the space 15 between the outer wall of the second section 82 of the pressure element and the inner wall of the receiving part body 5 provides room for the flexible second section 82 to expand when the head 3 is inserted.

A depth of the cylindrical recess 89 of the pressure element is smaller than a radius of the rod 6, so that the pressure element can be pressed down by means of screwing-in the inner screw 7, which presses onto the rod 6, which in turn presses onto the pressure element 8. The pressure element 8 is oriented in the receiving part body 5 such that its cylindrical recess 89 is aligned with the U-shaped recess of the receiving part body 5.

The material of which the components of the bone anchoring device are made is preferably a body compatible metal, such as stainless steel or titanium, or a body compatible alloy such as a nickel titanium alloy, in particular Nitinol. However, body compatible plastic materials, such as medical-grade polyether ether ketone (PEEK), can also be used.

In use, first, the pressure element 8 is introduced via the bottom opening 14 into the receiving part body 5 until it abuts against stop 17. This can be done either by the surgeon, or before so that the receiving part body is preassembled with the pressure element 8. Thereafter, the head 3 is introduced through the bottom opening and pushes the pressure element 8 upwards against stop 17. This is the insertion position, which allows the screw head 3 to be introduced through the opening 84 into the pressure element 8, thereby widening the hollow interior 83, or the legs 90 respectively, until the pressure element 8 snaps onto the head 3. This can be done either before screwing the threaded shaft 2 into the bone, or after having screwed in the threaded shaft 2 into the bone, to mount the receiving part body 5, with the pressure element inside, onto the head 3. When the head 3 is inserted, it can still pivot within the pressure element 8 if the flexible section 82 is not compressed. A plurality of bone anchoring devices may be implanted into the bone(s), for example, in the pedicles of adjacent vertebrae, and the rod 6 may be inserted into the bone anchoring devices, respectively. Angular positions of the receiving part bodies may then be adjusted. Finally, the set screw 7 for each bone anchoring device may be tightened, thereby pressing down the rod 6 onto the respective pressure elements, which are pressed down until the second portion 87 of the outer wall of the second section 82 of each pressure element engages with the narrowing portion 13 of the respective receiving part bodies. In this condition, the head of each bone anchoring device is clamped in an interior of the pressure element, so that it is locked in a desired angular position.

FIGS. 8a to 8d show various designs of the narrowing portion 13 of the receiving part body 5 and the portion 87 of the pressure element 8 which engages the narrowing portion 13 according to embodiments of the invention. FIG. 8a shows the two portions tapering lineally at substantially a same angle. This provides a substantially even pressure distribution between the second portion 87 of the pressure element 8 and the narrowing portion 13 of the receiving part body 5. FIG. 8b and FIG. 8c show two different designs where the respective portions are tapered at different angles. FIG. 8b shows a main contact area at a bottom of the narrowing portion 13, and FIG. 8c shows a main contact area at a top of the narrowing portion 13. FIG. 8d shows a tapering second portion 87 of the pressure element 8 and a rounded portion 13 of the receiving part body, wherein a curvature of the rounded portion is directed towards a center of the receiving part body 5. With such a configuration, a contact area positioned at the rounded portion can be achieved.

In FIGS. 9a and 9b a narrowing portion 13' of a modified example of a receiving part body 5 has a double spherical radius formed by two curved portions 13a, 13b on top of (i.e., adjacent to) each other, with a groove 13c therebetween. A curvature of the curved portions are directed towards the central axis M. Correspondingly, a modified pressure element 8' has at its lower end two invertedly curved portions 8a, 8b which correspond to the curved portions 13a, 13b, with a crest 8c therebetween, and an outer crest 8d at an outer yielding edge of the pressure element 8'.

As shown in FIG. 9a, when the pressure element 8' moves downward, its lower most edge 8d engages in the groove 13c. In this position there is a frictional clamping of the head 3, which still allows the head 3 to be pivoted upon exertion of a force, where this force is greater than a force needed to pivot the head 3 when the head 3 is introduced in an insertion position. This may be characterized as a pre-locking condition. As shown in FIG. 9b, by further pressing the pressure element 8' downward, the curvatures of the pressure element 8' engage with the corresponding curvatures of the narrowing portion 13' to finally lock the head 3.

Further modifications of the bone anchoring device are possible. For example, in one embodiment the pressure element 8 can have a recess corresponding to the cylindrical recess 89 described above, which may be U-shaped and provides legs extending above the rod. A dual part closure element can then be used to separately clamp the head and the rod. A device for preventing the pressure element from rotating can be provided (not shown). Such a device can be realised, for example, by crimp bores or by a pin extending from the wall into a recess (not shown) of the pressure element.

Further, in some embodiments, the abutment or stop 17, on which a pressure element may abut after it is inserted through the bottom opening and pushed further inwards, can be provided at other locations in the receiving part, for example, at the circular shoulder 16, which may then interact with a corresponding projecting part of the pressure element to provide an abutment for the pressure element.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
   a receiving part body having a first end, a second end, a substantially U-shaped recess at the first end forming a channel for receiving the rod, an accommodation space for accommodating a head of the bone anchoring element, and an opening at the second end below the accommodation space for introducing the head; and
   a pressure element configured to be arranged at least partially in the accommodation space, the pressure element comprising a first section configured to contact the rod when the pressure element is in the receiving part, and a second section having an expandable portion in which to insert and clamp the head, wherein the first section comprises a first region, the first region having a cross-section with a rounded outer profile that extends uniformly in an axial direction for the entire first region, and the pressure element has a slit with an open end at a free end of the second section and a closed end that extends into the first region of the first section of the pressure element;
   wherein when the pressure element is below the opening of the receiving part body with the first section positioned between the second section and the opening, said pressure element is insertable upwards through the opening at the second end of the receiving part body into the accommodation space.

2. The receiving part of claim 1, wherein the receiving part body comprises a narrowing portion near the opening, the narrowing portion configured to cooperate with a corresponding portion of the pressure element to clamp the head.

3. The receiving part of claim 2, wherein at least one of the narrowing portion of the receiving part body or the corresponding portion of the pressure element is tapered.

4. The receiving part of claim 3, wherein both the narrowing portion of the receiving part body and the corresponding portion of the pressure element are tapered.

5. The receiving part of claim 3, wherein the other one of the narrowing portion of the receiving part body or the corresponding portion of the pressure element is curved.

6. The receiving part of claim 2, wherein the narrowing portion of the receiving part body comprises two adjacent curved portions forming a groove therebetween, and the corresponding portion of the pressure element comprises two corresponding adjacent curved portions forming an inner crest therebetween and further comprising an edge crest along an outer edge of one of the two corresponding adjacent curved portions, wherein the edge crest is configured to snap into the groove in a first locking position of the pressure element, and the inner crest is configured to snap into the groove in a second locking position of the pressure element.

7. The receiving part of claim 1, wherein the receiving part body has a bore extending between the first and second ends, the bore including a hollow cylindrically shaped portion, and wherein the accommodation space is positioned between the opening and the hollow cylindrically shaped portion.

8. The receiving part of claim 7, wherein the pressure element includes a substantially cylindrically shaped portion having a diameter corresponding to a diameter of the hollow cylindrically shaped portion, such that the pressure element is moveable along a longitudinal axis of the receiving part body.

9. The receiving part of claim 7, wherein the accommodation space has a larger diameter than a diameter of the hollow cylindrically shaped portion.

10. The receiving part of claim 7, wherein the expandable portion has a diameter larger than a diameter of the hollow cylindrically shaped portion.

11. The receiving part of claim 1, wherein the first section of the pressure element has a diameter smaller than a diameter of the opening, and the second section of the pressure element has a diameter larger than the diameter of the opening.

12. The receiving part of claim 11, wherein the expandable portion is configured to be compressible for insertion through the opening.

13. The receiving part according to claim 1, wherein the expandable portion of the pressure element has a plurality of slits extending from the free end of the second section towards the first section.

14. The receiving part according to claim 13, wherein the slits extend into the first section.

15. The receiving part of claim 1, wherein in an insertion position, the pressure element is positioned in the receiving part body such that a space between an outer wall of the expandable portion and an inner wall of the accommodation space provides for widening of the expandable portion for inserting the head.

16. The receiving part of claim 1, further comprising a closure element wherein the receiving part body has a bore extending between the first and second ends, and a thread at the first end for engagement with the closure element for fixing the rod in the channel.

17. The receiving part of claim 1, wherein the first region of the pressure element has at least a portion positioned farther away axially from the free end of the second section than the closed end of the slit is from the free end of the second section.

18. The receiving part of claim 1, wherein an inner bore extends through the pressure element, and wherein at least a portion of the inner bore at the first region of the pressure element has a width that stays constant as the inner bore extends axially.

19. A method for coupling a rod to a bone anchoring element via a receiving part, the receiving part comprising a receiving part body having a first end, a second end, a substantially U-shaped recess at the first end forming a channel for receiving the rod, an accommodation space for accommodating a head of the bone anchoring element, and an opening at the second end below the accommodation space for introducing the head, and a pressure element configured to be arranged at least partially in the accommodation space, the pressure element comprising a first section configured to contact the rod when the pressure element is in the receiving part, and a second section having an expandable portion in which to insert and clamp the head, wherein the first section comprises a first region, the first region having a cross-section with a rounded outer profile that extends uniformly in an axial direction for the entire first region, and the pressure element has a slit with an open end at a free end of the second section and a closed end that extends into the first region of the first section of the pressure element, wherein when the pressure element is below the opening of the receiving part body with the first section positioned between the second section and the opening, said pressure element is insertable upwards through the opening at the second end of the receiving part body into the accommodation space, the method comprising:
  introducing the head through the opening into the pressure element, wherein the expandable portion of the pressure element expands in the accommodation space to accommodate the head;
  inserting the rod into the channel;
  adjusting an angular position of the receiving part with respect to the bone anchoring element to be aligned with the rod; and
  advancing a closure element in the substantially U-shaped recess towards the second end of the receiving part body, the closure element advancing the rod towards the second end, the rod advancing the pressure element towards the second end,
  wherein the closure element is advanced until it locks the relative positions of the rod and the bone anchoring element with respect to the receiving part.

20. The method of claim 19, further comprising inserting the bone anchoring element into a bone prior to introducing the head through the opening into the pressure element.

21. The method of claim 19, further comprising inserting the pressure element through the opening of the receiving part body prior to introducing the head through the opening into the pressure element.

22. A bone anchoring device comprising:
  a bone anchoring element comprising a shaft and a head;
  a receiving part for receiving a rod for coupling the rod to the bone anchoring element, the receiving part comprising:
    a receiving part body having a first end, a second end, a substantially U-shaped recess at the first end forming a channel for receiving the rod, an accommodation space for accommodating the head of the bone anchoring element, and an opening at the second end below the accommodation space for introducing the head; and
    a pressure element configured to be arranged at least partially in the accommodation space, the pressure element comprising a first section configured to contact the rod when the pressure element is in the receiving part, and a second section having an expandable portion in which to insert and clamp the head, wherein the first section comprises a first region, the first region having a cross-section with a rounded outer profile that extends uniformly in an axial direction for the entire first region, and the pressure element has a slit with an open end at a free end of the second section and a closed end that extends into the first region of the first section of the pressure element;
  wherein when the pressure element is below the opening of the receiving part body with the first section positioned between the second section and the opening, said pressure element is insertable upwards through the opening at the second end of the receiving part body into the accommodation space.

* * * * *

UNITED STATES PATENT AND TRADEMARK OFFICE
CERTIFICATE OF CORRECTION

PATENT NO. : 9,895,172 B2
APPLICATION NO. : 14/878809
DATED : February 20, 2018
INVENTOR(S) : Lutz Biedermann et al.

It is certified that error appears in the above-identified patent and that said Letters Patent is hereby corrected as shown below:

In the Claims

Column 7, Line 31, Claim 16, delete "element" and insert -- element, --

Signed and Sealed this
Fourteenth Day of May, 2019

Andrei Iancu
*Director of the United States Patent and Trademark Office*